United States Patent
Tuttemann et al.

(10) Patent No.: US 11,179,288 B2
(45) Date of Patent: Nov. 23, 2021

(54) LEG ORTHOSIS AND ORTHOSIS

(71) Applicant: OTTO BOCK HEALTHCARE GMBH, Duderstadt (DE)

(72) Inventors: Markus Tuttemann, Waltrop (DE); Carsten Vogel, Duderstadt (DE)

(73) Assignee: OTTOBOCK SE & CO. KGAA

( * ) Notice: Subject to any disclaimer, the term of this patent is extended or adjusted under 35 U.S.C. 154(b) by 636 days.

(21) Appl. No.: 15/321,567

(22) PCT Filed: Jun. 24, 2015

(86) PCT No.: PCT/EP2015/064275
§ 371 (c)(1),
(2) Date: Dec. 22, 2016

(87) PCT Pub. No.: WO2015/197704
PCT Pub. Date: Dec. 30, 2015

(65) Prior Publication Data
US 2017/0156963 A1   Jun. 8, 2017

(30) Foreign Application Priority Data

Jun. 24, 2014 (DE) .......................... 102014009028.0

(51) Int. Cl.
*A61H 3/00* (2006.01)
*A61F 5/01* (2006.01)
(Continued)

(52) U.S. Cl.
CPC ............... *A61H 3/00* (2013.01); *A61F 2/605* (2013.01); *A61F 2/64* (2013.01); *A61F 2/6607* (2013.01);
(Continued)

(58) Field of Classification Search
CPC ............ A61F 5/0102; A61F 2005/0144; A61F 2005/0155; A61H 3/00; A61H 1/00;
(Continued)

(56) References Cited

U.S. PATENT DOCUMENTS 3,449,769 A * 6/1969 Mizen ....................... A61F 2/54
601/23
4,964,628 A * 10/1990 Poplawski ............. A61F 5/0102
482/51
(Continued)

FOREIGN PATENT DOCUMENTS

CN          1440857 A    9/2003
CN        101565064 A   10/2009
(Continued)

OTHER PUBLICATIONS

Schmidt, Henning, "HapticWalker—A novel haptic device for walking simulation," Fraunhofer Institute IPK, Proceeding of EuroHaptics 2004, Munich, Germany, Jun. 5-7, 2004, pp. 60-67.
(Continued)

*Primary Examiner* — Camtu T Nguyen
(74) *Attorney, Agent, or Firm* — Holland & Hart LLP

(57) ABSTRACT

A leg orthosis including a securing device for securing the leg orthosis to the body of a orthosis user and at least one articulation device by means of which a first orthosis component, which can be fixed to an extremity of the user, is mounted such that it can pivot with respect to the securing device. The articulation device includes at least three joints, which respectively comprise at least one pivot axis, and each pivot axis intersects at a common point.

19 Claims, 8 Drawing Sheets

(51) Int. Cl.
*A61F 2/60* (2006.01)
*A61F 2/64* (2006.01)
*A61F 2/66* (2006.01)

(52) U.S. Cl.
CPC .... *A61F 5/0102* (2013.01); *A61F 2005/0144* (2013.01); *A61F 2005/0155* (2013.01)

(58) Field of Classification Search
CPC ...... A61H 1/02; A61H 1/0237; A61H 1/0244; A61H 1/0255; A61H 1/0262; A61H 1/0266; A61H 2001/0248; A61H 2001/0251; A61H 2201/0107; A61H 2201/0157; A61H 2201/1207; A61H 2201/1215; A61H 2201/123; A61H 2201/149; A61H 2201/1628; A61H 2201/163; A61H 2201/164; A61H 2201/1642; A61H 2201/165; A61H 2201/1652; A61H 2201/1657; A61H 2201/1676; A61H 2201/5002; A61H 2201/5007; A61H 2201/5053; A61H 2203/0406; A61H 2205/088; A61H 2205/102; A61H 2205/12; A61H 2201/1671; A61H 2201/1673; A61H 2201/0192; A61H 2201/1635; A61H 2201/1638; A61H 2201/1645; A61H 2201/1647
See application file for complete search history.

(56) References Cited

U.S. PATENT DOCUMENTS

| | | | |
|---|---|---|---|
| 9,101,451 | B2 | 8/2015 | Chugunov |
| 2004/0025619 | A1 | 12/2004 | Nakamura et al. |
| 2007/0056592 | A1* | 3/2007 | Angold ............. A61H 3/00 128/845 |
| 2007/0225620 | A1 | 9/2007 | Carignan et al. |
| 2010/0204627 | A1 | 8/2010 | Kazerooni et al. |
| 2012/0172769 | A1 | 7/2012 | Garrec |
| 2013/0226048 | A1 | 8/2013 | Unluhisarcikli et al. |

FOREIGN PATENT DOCUMENTS

| | | |
|---|---|---|
| CN | 102499857 A | 6/2012 |
| CN | 102711678 A | 10/2012 |
| DE | 19645494 A1 | 6/1997 |
| DE | 202013009698 U1 | 1/2014 |
| EP | 2153804 A1 | 2/2010 |
| EP | 2163226 A1 | 3/2010 |
| JP | 2009-178253 | 8/2009 |
| WO | 2013186705 A2 | 12/2013 |

OTHER PUBLICATIONS

Hocoma, LokomatPro, Functional Robotic Gait Therapy, 16 pages (no date).
PCT International Search Report for PCT International Patent Application No. PCT/EP2015/064275, dated Dec. 10, 2015.

* cited by examiner

LEG ORTHOSIS AND ORTHOSIS

TECHNICAL FIELD

The invention relates to a leg orthosis and an orthosis comprising a securing device for fixing the orthosis or leg orthosis to a trunk of the body of an orthosis user and at least one articulation device, by way of which a first orthosis component, which can be fixed to an extremity of the orthosis user, is mounted pivotably relative to the securing device. The orthosis is designed in particular as a leg or shoulder orthosis and is intended to be used as an exoskeleton for rehabilitation measures.

BACKGROUND

After a stroke or neurological disorders or injuries, it is advantageous to initiate early rehabilitation, in order to counteract restrictions in mobility, in particular including in the ability to walk. There is a positive correlation between the intensity of the training and the result of the rehabilitation. It is therefore advantageous to begin intensive rehabilitation measures as early as possible, which however at the present time requires an appropriately trained person. Manual gait therapy, which can be carried out in a supportive sense on a treadmill, is on the one hand limited in terms of time due to the necessary therapist and on the other hand leads to correspondingly short therapy sessions.

There are permanently installed systems with a treadmill, such as the Locomat® from the company Hocoma or the so-called "Haptic Walker" from the Fraunhofer Institute for Production Systems and Design Technology, which is designed as a robot-assisted walking simulator and is used especially for motor gait rehabilitation in the case of stroke patients and patients with incomplete paraplegia or an intracranial trauma.

The equipment that is already known is problematic in terms of the high operational expenditure and the restricted mobility or stationary arrangement of the equipment.

EP 2 163 226 A1 relates to an exoskeleton intended to be worn during skiing. The exoskeleton is fixed to the ski boot, the lower leg, the upper leg and the hip. At the height of the respective natural joints, articulation devices are arranged. In the hip area, a double joint is arranged. The articulation devices between the upper leg and the lower leg are connected by way of a coupling in the form of a clutch mechanism. A sensor detects the movement and/or pressure on parts of the ski and transmits corresponding signals to the coupling. In the presence of potential overloading, the coupling is completed, so that forces can be directed around the natural joint by way of the exoskeleton. With such an exoskeleton, no natural gait movements are performed.

DE 20 2013 009 698 U1 describes parallel kinematics for an orthosis or an exoskeleton with lateral coupling locations, the idealized joint axes of the human extremity not extending coaxially in relation to the joint axes of the orthosis or the exoskeleton.

SUMMARY

The object of the present invention is to provide an orthosis with which a correct movement pattern, in particular gait behavior, can be achieved at the same time as increased mobility.

This object is achieved according to the invention by a leg orthosis with the features of the main claim and an orthosis with the features of the alternative independent claim; advantageous configurations and developments of the invention are disclosed in the subclaims, the description and the figures.

The leg orthosis comprising a securing device for fixing the leg orthosis to a trunk of the body of an orthosis user and at least one articulation device, by way of which a first orthosis component, which can be fixed to an extremity of the orthosis user, is mounted pivotably relative to the securing device, provides that the articulation device has at least three joints, which respectively have at least one pivot axis and the respectively at least one pivot axes intersect at a common point, the pivot axes forming at least three independent degrees of freedom at the common point of intersection. The configuration of the articulation device with three pivot axes and a common point of intersection makes it possible to produce a movement behavior of the orthosis that corresponds to a natural joint in the form of a ball-and-socket joint. It is consequently possible to replicate a ball-and-socket joint lying within the body by external joints, so that on the one hand the orthosis can perform the necessary supporting and guiding function and on the other hand a physiologically correct movement behavior can be achieved by the orthosis user. The configuration of the articulation device with three joint axes intersecting at a point produces a ball-and-socket joint in a position, that is to say within the body, in which a direct mechanical realization of the joints would not be possible if the joints were mounted outside, and consequently the natural movement would be restricted. When mention is made hereafter of the orthosis, the statements relate both to leg orthoses and to shoulder orthoses or to orthoses in general; if specific properties are explained, the respective embodiment is dealt with separately. When there are three pivot axes which intersect at a common point, three rotational degrees of freedom that are independent of one another are formed at the common point of intersection of the three pivot axes of the joints, so that a movement of the orthosis can be realized as in the case of a ball-and-socket mounting.

The articulation device may be assigned at least one drive or energy store, in order to make the orthosis pivotable in at least one plane and actively supportable. As a result, it is advantageously possible to support the orthosis user during walking, for example during the flexion and extension within the sagittal plane, that is to say when raising and lowering the knee or raising or lowering the arm or another part of the extremity. In principle, it is also possible to provide a number of drives, which are effective about a number of or all of the pivot axes of the joints. Apart from a motor drive with an external energy source, for example a battery or a rechargeable battery, energy stores may also be assigned, for example springs or the like, to provide a support for movement.

The degrees of freedom of the pivot axis of at least one of the joints of the articulation device advantageously do not influence the degrees of freedom of the other joint, so that there is no co-coupling of movements in the case for example of pure flexion or extension or adduction or abduction or in the case of internal rotation or external rotation. In one configuration of the invention, all of the degrees of freedom are in a form in which they are decoupled from one another; a variant of the invention provides that only one joint is decoupled from the other joints, while the degrees of freedom of the other joints can influence one another. If for example one axis is driven, the drive does not exert moments on the other axes of the articulation device or the orthosis. The non-driven axes can influence one another, but moments about these axes have no effect on the driven axis.

In particular in the case of the configuration as a leg orthosis, the securing device is advantageously designed for fixing the orthosis to the pelvis, the area of the abdomen or the waist, the first orthosis component being designed as an upper leg rail or upper arm rail. The arrangement of the orthosis with the securing device on the pelvis, the area of the abdomen or the waist makes it possible to position the securing device additionally in a frame or framework, so that it is possible also to support and bear the weight of the trunk of the body, so that it is possible to provide relief from the weight of the orthosis during movement. The orthosis user does not have to bear his or her entire body weight during walking or movement; rather, it is possible to absorb part of the weight by way of the securing device.

The pivot axes of the joints of the articulation device preferably intersect at the point of rotation of the ball-and-socket joint of the orthosis user, that is to say in the hip joint if the orthosis is designed as a leg orthosis or in the shoulder joint if the orthosis is designed as a shoulder-arm orthosis, the possibilities that there are for making compensations when fixing the orthosis to the orthosis user, the play that occurs and the variability of the human body meaning that it is sufficient if the pivot axes extend through an imaginary spherical body that corresponds in size to the articular condyle of the hip joint or of the shoulder joint.

The first orthosis component may have a number of portions that are connected to one another in an articulated manner, each portion being connected to the other portion by a joint. One portion is coupled to the securing device, a further portion may be connected in an articulated manner to a further orthosis component. The articulated connection of the first orthosis component, which is fixed to the upper leg or upper arm of the orthosis user, makes it possible to support the complete leg or the entire arm by way of the orthosis, that is to say the lower leg and the foot or the lower arm and the hand. The further orthosis component or the further orthosis components is/are formed such that it/they can be fixed to the respective extremity, the pivot axes of the joints between the further orthosis components or between the first orthosis component and the orthosis component adjoining it being in line with the joint axes of the respective extremity, that is to say the joint axes of the natural joints, when the leg orthosis is in the fitted state, in order not to bring about any impairment of the natural mobility of the respective extremity as a result of the orthosis component.

The pivot axes of the joints of the articulation device may have in each case one degree of freedom, preferably in each case precisely one degree of freedom, the degrees of freedom not extending co-linearly in relation to one another, so that by adding the degrees of freedom a movement of the extremity, and consequently also of the orthosis, that corresponds to that of a ball-and-socket joint can be achieved.

One degree of freedom of a pivot axis of the articulation device is advantageously oriented in the sagittal plane, whereas the two other degrees of freedom of the pivot axes of the joints of the articulation device are oriented in the frontal plane, in order to produce an axis projected vertically at the point of rotation of the joint.

If restrictions of movement are necessary or the full range of movement of the natural joints is not to be used, the pivoting ranges of the joints are adjustably formed, at least the pivoting range of one joint. This makes it possible for a step-by-step adaptation to the respective maximum radii of movement to be achieved, so that allowance can be made for medically necessary restrictions of movement on the one hand and progresses in therapy on the other hand.

A development of the invention provides that at least two of the at least three pivot axes are not aligned orthogonally in relation to one another. This makes it possible that the joints can be arranged within the body alongside the extremities or the trunk of the body, at locations that make it possible to bear the weight of the orthosis. In the case of axes that are not aligned orthogonally in relation to one another, combined movements can be performed by one joint without other joints having to be moved along with it; the orientation of the axes can consequently be adapted to the movements of the orthosis user, since it is in the rarest cases that an isolated movement in precisely one plane about precisely one axis lying in this plane is performed. A coupling of the joints by way of force transmission devices preferably does not take place.

The orthosis according to the invention comprising a securing device for fixing the orthosis or leg orthosis to a trunk of the body of an orthosis user and at least one articulation device, by way of which a first orthosis component, which can be fixed to an extremity of the orthosis user, is mounted pivotably relative to the securing device, the articulation device having a least three joints, which respectively have a pivot axis, and the pivot axes intersecting at a common point, provides that the degrees of freedom of a pivot axis of at least one joint of the articulation device do not influence the degrees of freedom of the pivot axes of the other joints, whereby it is possible to make a drive become effective about one axis without causing unwanted movements or introducing unwanted movements when muscles provide a natural means of driving a movement. The statements made above in relation to leg orthoses or shoulder-arm orthoses apply correspondingly to the orthosis according to the invention.

The pivot axes of the joints preferably intersect at a common point and form at least three independent degrees of freedom at the common point of intersection.

BRIEF DESCRIPTION OF THE DRAWINGS

Exemplary embodiments of the invention are explained in more detail below on the basis of the accompanying figures, in which.

DETAILED DESCRIPTION

Figure 1:
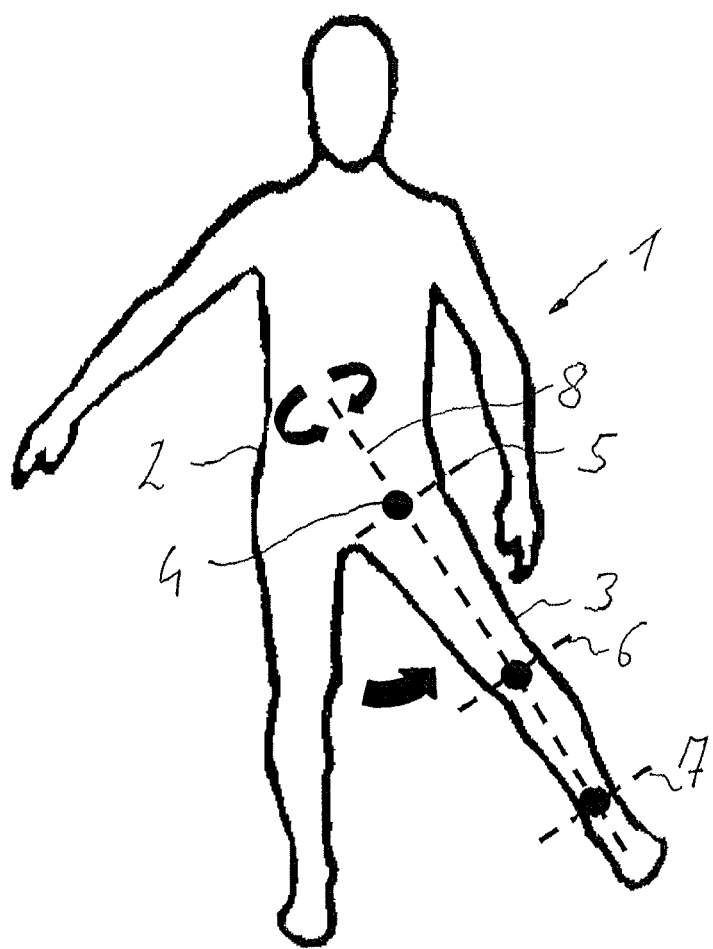
FIG. 1 shows a schematic representation of a human body with joint axes.

FIG. 1 shows in a schematic representation an orthosis user 1 with a trunk of the body 2 and two lower extremities 3. The left extremity 3 of the orthosis user 1 is abducted, that is to say pivoted outwardly in the frontal plane.

The pivoting takes place in this case about the axis 4, which extends through the joint, which is not represented any more specifically. Depicted in the area of the knee of the lower extremity is a knee axis 6, which enables a flexion and extension of the lower leg; an ankle axis 7 enables a plantar flexion and a dorsal extension. Also depicted is the leg axis 8, about which an internal rotation or external rotation of the lower extremity 3 takes place, so that, with a leg extended, the foot can be turned with the tip of the foot in the outward or inward direction.

Figure 2:
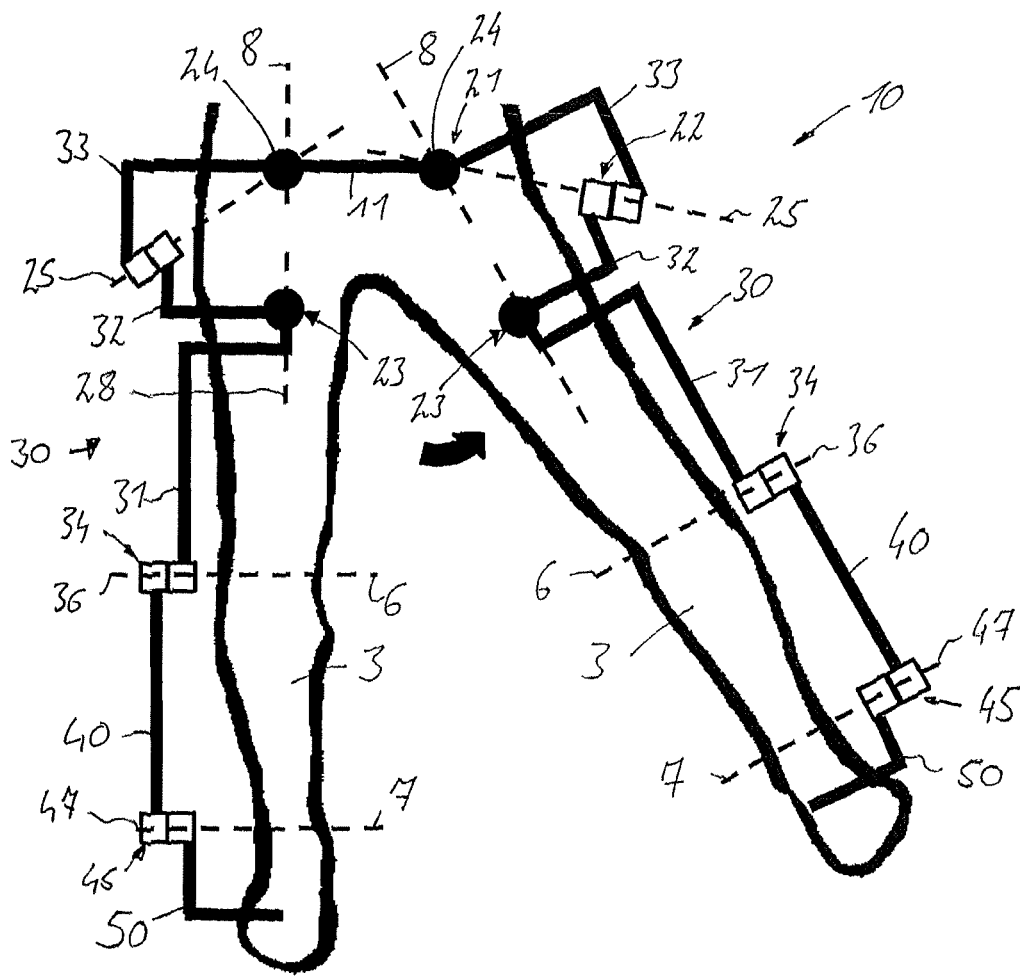
FIG. 2 shows a schematic representation of a fitted orthosis.

FIG. 2 shows in a partial representation the stance of the orthosis user 1 according to FIG. 1 with the fitted orthosis 10, the orthosis 10 being represented schematically. The orthosis 10 has a schematically represented securing device 11, which is designed for fixing to the trunk of the body 2 of the orthosis user 1. The securing device 11 may be designed as a sleeve, shell or multipart sheath, which can be fixed to the orthosis user 1 around the trunk of the body 2, for example in the area of the waist, the hips or the pelvis. The fixing may take place by way of straps, clips, clasps or adjustable securing elements. For each extremity 3, a first orthosis component 30 is secured in an articulated manner on the securing device 11, which also extends in the area of the pelvis. The first orthosis component 30 has three portions 31, 32, 33, which are connected to one another by way of joints 22, 23. The portion 33 closest to the securing device 11, also known as the securing portion, is likewise mounted on the securing device 11 by way of a joint 21, so that the entire first orthosis component 30 is pivotably mounted on the securing device 11 by way of three joints 23, 22, 21. The first orthosis component 30 is fixed to the upper leg, advantageously in the area of the upper leg of the orthosis user 1, by way of conventional sleeves or straps 60, which are only represented schematically. Adjoining distally in relation to the upper leg rail 31 there is a lower leg rail 40, which is pivotably coupled to the upper leg rail 31 by way of an orthosis knee joint 34. Adjoining the distal end 40 of the lower leg rail there is an orthosis ankle joint 45, which couples the lower leg rail 40 to a foot rail 50 in an articulated manner. Both the foot rail 50 and the lower leg rail 40 are secured to the respective part of the lower extremity 3 by way of securing means, for example straps 60, sleeves, hook and loop fasteners or the like. The joint axes 36, 47 of the orthosis knee joint 34 and of the orthosis ankle joint 45 are formed such that they are co-linear in relation to the joint axes 6, 7 of the natural knee joint or ankle joint, so that a natural movement of the lower extremities 3 can take place. In the case of the orthosis ankle joint 45, also only a plantar flexion or dorsal extension is envisaged.

The articulation device 20 with the three joints 21, 22, 23 is constructed in such a way that the joint axes 24, 25, 28 of the respective joints 21, 22, 23 intersect at a common point 100, the point of intersection of the joint axes 24, 25, 28 corresponding to the center of rotation of the natural hip joint. In this case it is not absolutely necessary that the axes 24, 25, 28 meet at precisely one geometrical point, it may be sufficient if all of the axes 24, 25, 28 extend through a spherical area that corresponds to the articular condyle of the hip joint.

In the exemplary embodiment represented, all of the joint axes 24, 25, 28, 36, 47 of the joints 21, 22, 23, 34, 45 of the respective unilateral orthosis are provided with only precisely one rotational degree of freedom. The joint axes 24, 25, 28 of the articulation device 20 of the first orthosis component 30 intersect at precisely one point, which lies at the center of rotation of the natural hip joint, the axis of rotation 24 of the first point 21 extending perpendicularly to the frontal plane, so that an abduction or adduction is possible. The pivot axis 25 of the second joint 22 serves predominantly for the extension or flexion of the upper leg and represents a point of rotation of the hips, which is necessary for the raising and lowering of the knee joint. The third joint 23, which is arranged below the natural hip joint, forms an axis of rotation 28, which extends substantially co-linearly in relation to the leg axis 8, and consequently enables an internal rotation or external rotation of the foot or of the entire lower extremity.

The respective rotational degrees of freedom of the pivot axes 24, 25, 28 of the articulation device 20 do not influence one another and are aligned in relation to one another in such a way that the natural movement of the hip joint over a wide pivoting range of the lower extremity 3 is enabled, in particular an abduction and adduction and also an internal rotation and external rotation of the respective lower extremity 3.

Figure 3:
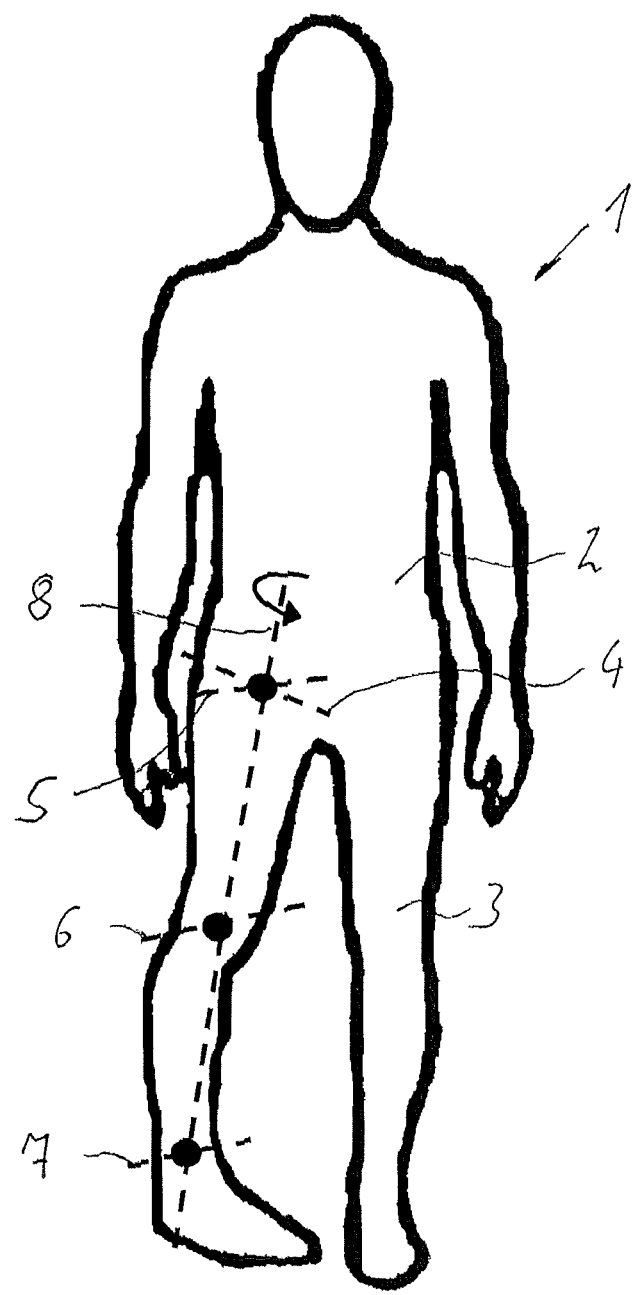
FIG. 3 shows a variant of FIG. 1.

FIG. 3 shows an orthosis user 1 without an orthosis, with an inwardly rotated right extremity 3. The orientation of the respective axes is depicted; the ankle joint axis 7 and the knee joint axis 6 extend approximately parallel to one another, the leg axis 8 enables the internal rotation and external rotation of the foot, two further hip axes, to be specific the hip axis 4, which lies in the sagittal plane and enables an abduction and adduction of the lower extremity 3, and the hip axis 5, which lies in the frontal plane and enables an extension and flexion of the lower extremity 3, intersect in the hip joint.

Figure 4:
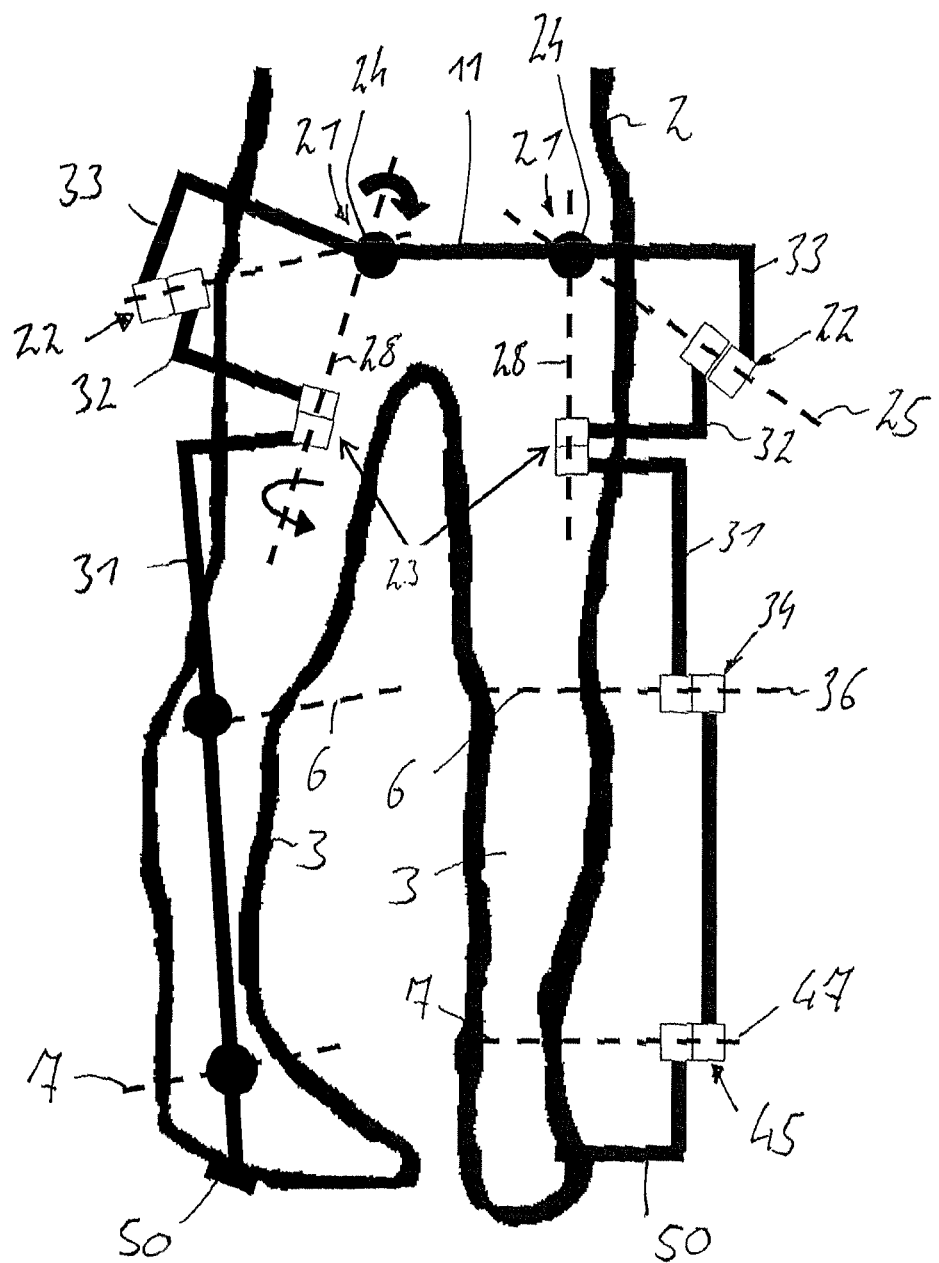
FIG. 4 shows a representation of a fitted orthosis in the position according to FIG. 1.

FIG. 4 shows a view of a detail of the position according to FIG. 3 with the orthosis 10 fitted. The internal rotation of the right extremity 3 is achieved predominantly by a tilting about the pivot axis 24 of the right first joint 21 and by a turning about the pivot axis 28 of the third joint 23. The superposing of the rotational movements in the two joints 21, 23 makes it possible to enable an internal rotation and accordingly also an external rotation by way of a set-down foot part 50, whereby it is readily possible with the orthosis to walk in a curve without performing a circumduction, which would result in an unphysiological gait pattern. Furthermore, FIG. 4 reveals that the pivot axis 28 of the third joint 23 is not oriented orthogonally in relation to the pivot axes 24, 25 of the first and second joints, but has a obliquely slanting position in relation to the other pivot axes 23, 24. The slanted pivot axis 28 of the third joint 23 makes it possible to perform a movement of the lower extremity in two planes, to be specific a leg rotation and an abduction or adduction. In the event that only an internal rotation or external rotation of the leg is desired, the concurrently initiated abduction or adduction is compensated in the rotary joint 21 that is movable exclusively in this plane, without the extremity that is located in the orthosis performing an abduction or adduction or being forced into such a movement. The orthosis therefore guides the leg correctly in the movement; the non-identical orientation of the pivot axes 24, 25, 28 in relation to the ideal movement axes of the leg is compensated within the orthosis, the second rotary joint 22 not being involved in a leg rotation and being decoupled from the two other rotary joints 21, 23.

The third joint 23 is arranged below the natural hip joint and is thus positioned in relation to the hip joint in the posterior and distal directions in such a way that it is located on the rear side of the upper leg and at a distance from the upper leg in the posterior direction. A co-linear alignment of the pivot axis 28 of the third joint 23 in relation to the leg axis 8 that enables the internal rotation or external rotation of the foot is not possible, since for this purpose the third rotary joint 23 would have to be arranged below the foot or else a parallel alignment of the pivot axis 28 would extend at a distance from the axis of rotation, which would prevent the pivot axes 24, 25, 28 from intersecting at a common point 100.

Figure 5:
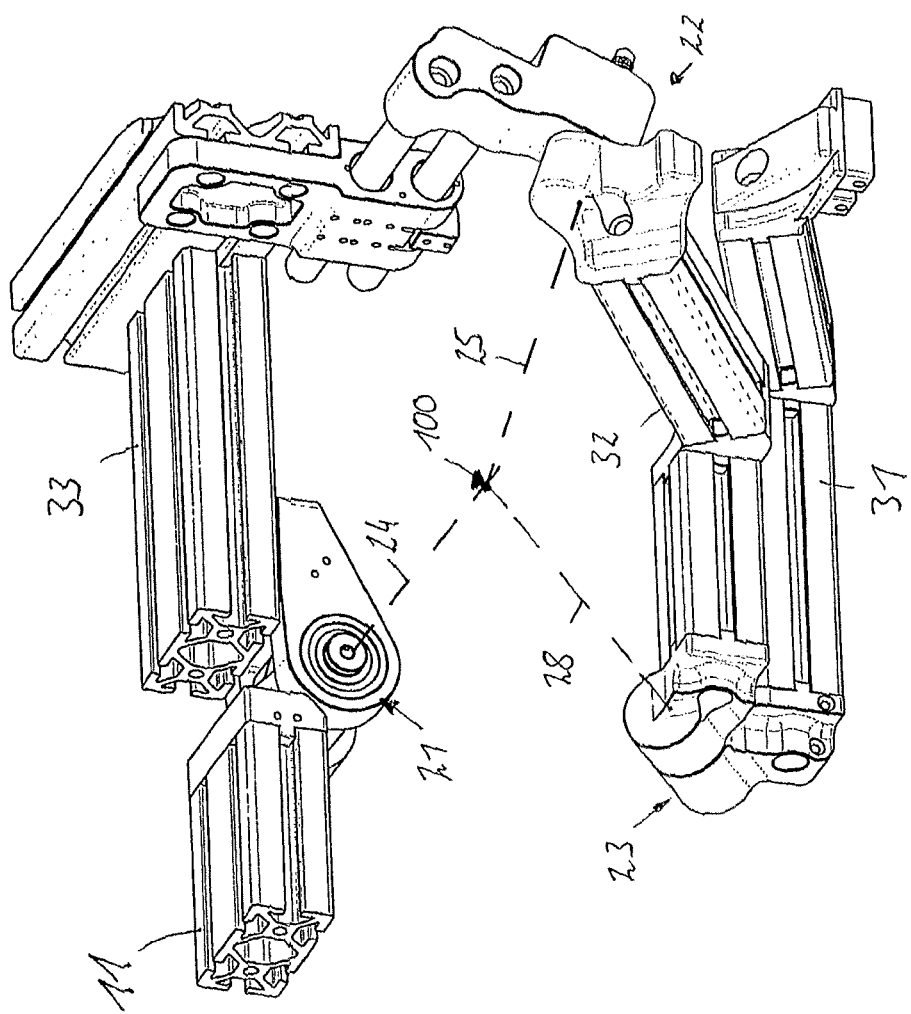
FIG. 5 shows a representation of a detail of an articulation device with parts of a securing device.

FIG. 5 shows a representation of a detail of the articulation device 20 with three joint portions 31, 32, 33, which are respectively connected to one another by way of joints 22, 23. The securing element 11 is partially represented and represents at the same time a connection between the respectively first joints 21, the pivot axes 24 of which enable an abduction and adduction of the lower extremity.

It can be seen in FIG. 5 that the respective pivot axes 24, 25, 28 of the joints 21, 22, 23 intersect at a common point 100, which lies within the orthosis user;

therefore, the virtual joint is projected into the point of rotation of the natural hip joint. This makes it possible to bring about a complete and natural mobility within the hips. All of the joints 21, 22, 23 of the articulation device 20 have in each case only one degree of freedom, to be specific a rotational degree of freedom, the pivot axis 24 of the first joint 21, which connects the first orthosis component 30 to the securing device 11, lying in the sagittal plane, while the two other pivot axes 25, 28 lie substantially in the frontal plane, the degrees of freedom of the pivot axes 24, 25, 28 of the joints 21, 22, 23 of the articulation device 20 not influencing one another, that is to say being decoupled from one another In FIG. 5, the configuration of part of an orthosis for a left leg is represented. The first rotary joint 21 is positioned such that its pivot axis 24 is positioned substantially at the same height as the natural hip joint, whereas the second joint 22, which is predominantly responsible for the flexion and extension, is arranged slightly below the height of the natural hip joint and consequently below the horizontal plane that extends through the first pivot axis 24. The rotary joint 22 may also lie at the same level as or above the natural hip joint. The second pivot axis 25, which extends through the second rotary joint 22, intersects the first pivot axis 24 at the common point 100; the second pivot axis 25 consequently extends obliquely upward, oriented in the direction of the common point 100.

The third pivot axis 28 of the third joint 23 preferably lies within a sagittal plane that extends through the first pivot axis 24. However, even if they extend outside such a sagittal plane, the angle between the two axes 24, 28 is an acute angle, so that it is possible to position the third joint 23 below and behind the hip joint and below the pelvis of the orthosis user.

As a result of the positioning of the second rotary joint 22 below the horizontal plane that extends through the common point 100, a likewise acute angle is obtained between the pivot axes 25, 28 of the second and third joints 22, 23. All three axes 24, 25, 28 are consequently not orthogonal to one another.

In all of the joints 21, 22, 23, 34, 45, pivoting range stops can be adjustably formed, in order in the case of physiological restrictions or necessary therapeutic restrictions to set a limitation or make an adaptation of the maximum pivoting angles.

In addition, it is possible that at least one articulation device is assigned a drive or an energy store, for example a motor, in order to assist the orthosis user in the movement, for example in order to bring about an extensional flexion of the upper leg and/or of the lower leg.

Figure 6:
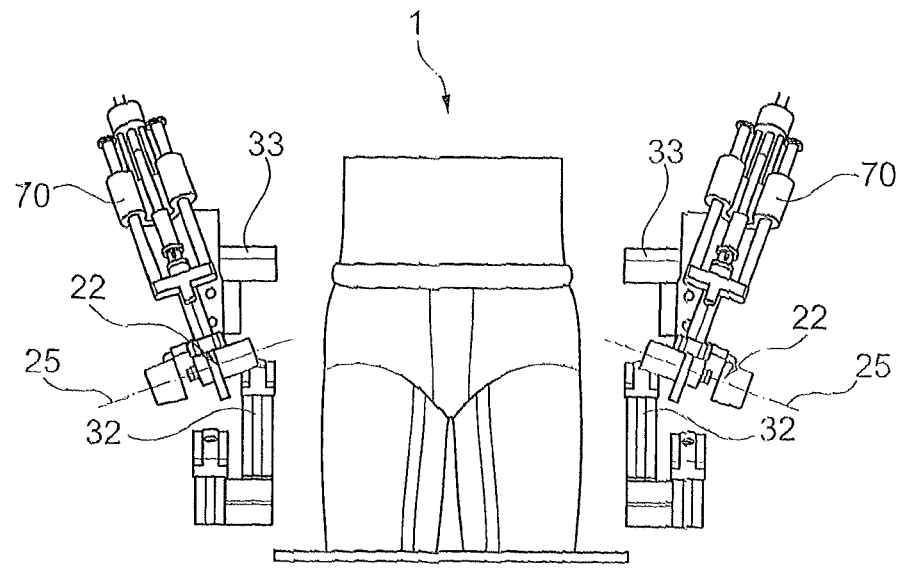
FIG. 6 shows a partial view of an embodiment of the invention.

In FIG. 6, a partial view of the orthosis on an orthosis user 1 is represented in a frontal view. Apart from the securing portion 33 and a joint 22, the pivot axis 25 of which substantially enables a flexion and extension of the hip and connects the securing portion 3 to the following portion 32, provided on both sides of the orthosis user 1 is a drive 70, by way of which the articulation device 30 can be moved with the secured to the upper leg about the pivot axis 25, in order to facilitate for the patient a flexion and extension in the hip joint.

Figure 7:
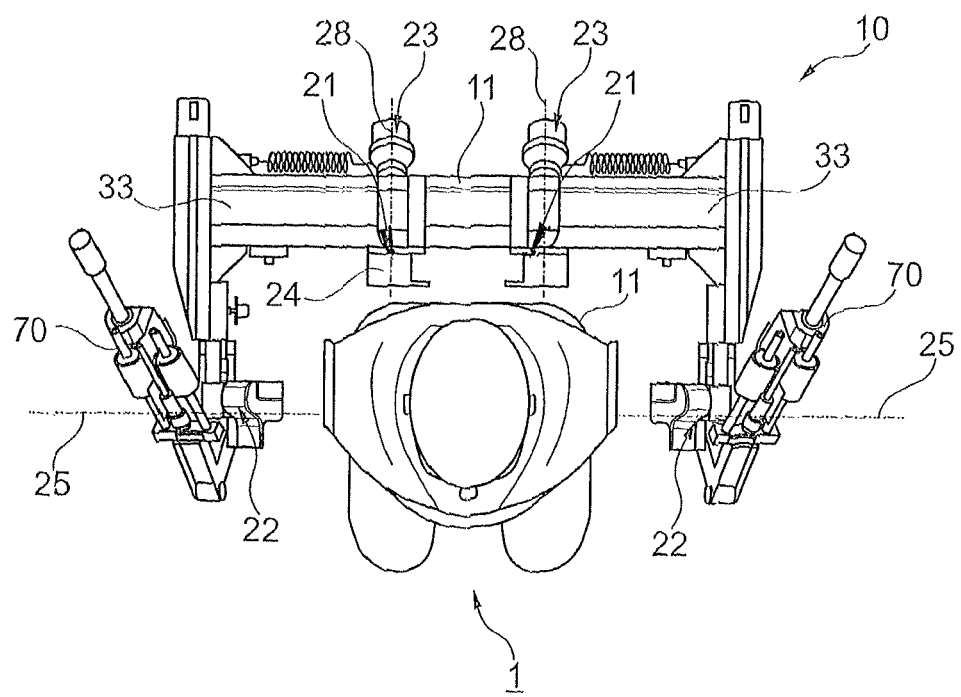
FIG. 7 shows a plan view of an orthosis user with a fitted orthosis.

FIG. 7 shows a plan view of an orthosis 10 fitted to an orthosis user 1; the securing means in the form of a rear sleeve are fixed to the orthosis user 1 by way of an abdominal strap. It can be seen in the figure that the pivot axis 25 of the joint 25 arranged laterally alongside the orthosis user 1 in the initial position extends substantially in the frontal plane and passes the natural hip joint, so that the drives 70, which are coupled to the joint portions 33, 32, can assist or bring about the flexion both of the right lower extremity and of the left lower extremity. It can similarly be seen in the plan view that the joint 21, which connects the securing portion 32 to the securing device 11, is arranged behind the prosthesis user and the pivot axis 24 points horizontally forward, substantially in the sagittal plane, in order to enable an abduction or adduction of the lower extremity. For this purpose, the respectively outer portion of the connecting portion 33 is raised or lowered.

In the plan view of FIG. 7 it can similarly be seen that the third joint 23, which is arranged distally both in relation to the first joint 21 and in relation to the second joint 22, is positioned behind the orthosis user 1 and forms an obliquely upwardly slanting pivot axis 28, which likewise lies substantially in the sagittal plane of the respective extremity and intersects with the two other axes of rotation 24, 25 of the two other joints 21, 22 in the area of the natural hip joint.

Figure 8:
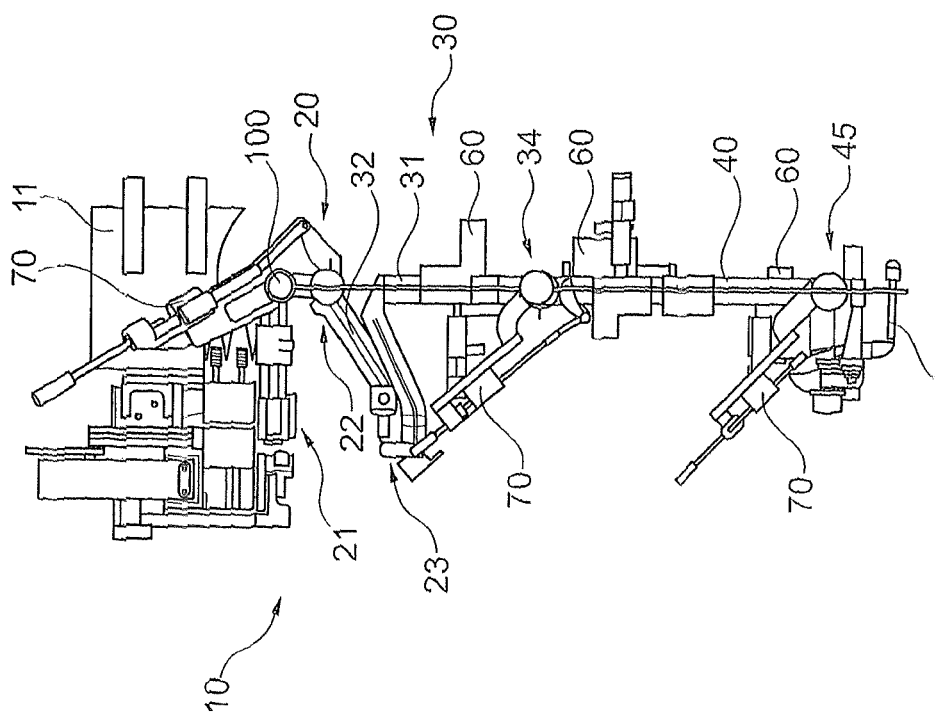
FIG. 8 shows a side view of an orthosis in the initial state.

FIG. 8 shows the orthosis 10 in an initial state in a side view. The securing device 11 with the orthosis 10 secured thereto is designed in the form of a sleeve, which can be fixed to the trunk of the body by way of hook and loop fasteners in the form of straps. The upper leg rail 31 of the first orthosis component 30, which can be fixed to the upper leg by way of a strap that is arranged in a sleeve enclosing the upper leg, can similarly be seen. Arranged below the orthosis knee joint 34 is a lower leg sleeve 60; arranged in the area of the orthosis ankle joint 45 is an ankle sleeve 60, to fix the lower leg to the lower leg rail 40. By way of the orthosis ankle joint 45, the foot part 50 is pivotably connected to the lower leg rail 40. Apart from a dorsal extension or plantar flexion about the orthosis ankle joint 45, a pivoting of the foot part 50 may additionally take place about a substantially horizontally oriented pivot axis that is oriented in the sagittal plane.

It can be seen from FIG. 8 that a number of drives 70, which respectively enable a flexion or extension of the respective orthosis component, are assigned to the orthosis. A drive 70 is arranged between the securing portion 33 and the central portion 32, in order to enable a flexion of the upper leg about the pivot axis of the joint 22. Additionally positioned on the upper leg rail 31 is a further drive 70 for the flexion or extension of the lower leg rail 40 relative to the upper leg rail 31 about the orthosis knee joint 34. For the flexion about the ankle joint axis, a third drive 70 is arranged on the lower leg rail 40, so that the essential movements of walking can be initiated or assisted by the drive 70.

It can be seen from the side view according to FIG. 8 that the first joint 21, and consequently also the first pivot axis 24, which enables the abduction and adduction of the leg, lies at a common height level with the common point 100 or the virtual hip joint 100. The second rotary joint 22, on the pivot axis 25, which is primarily responsible for the extension and flexion, lies below the common point 100, that is to say distally offset from the first pivot axis 24; the joint axis 25 may however also lie at the same height or above the common point 100. The third joint 23 additionally lies distally in relation to the second rotary joint 22 or offset in relation to the pivot axis 25, and consequently below the pelvis, approximately midway between the common point 100 and the orthosis knee joint 34.

Figure 9:
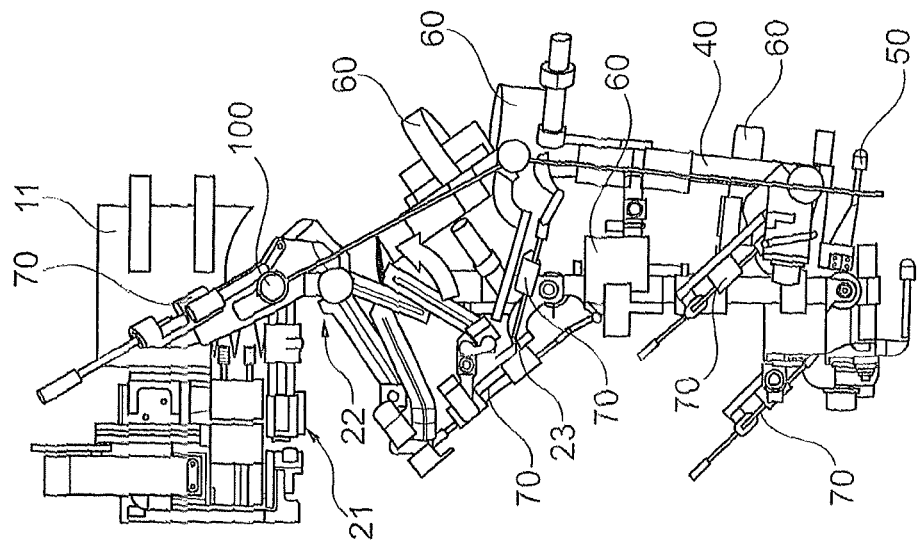
FIG. 9 shows a side view of the orthosis with the right leg raised.

FIG. 9 shows the configuration of the orthosis 10 with a position of the right lower extremity flexed about the pivot axis 25. A pivoting takes place about the notional hip joint 100, that is to say about the point at which the three axes of the articulation device 20 intersect. To bring about a virtually natural movement, at the same time the orthosis knee joint 34 is flexed, so that the lower leg rail 40 remains substantially perpendicularly oriented.

Figure 10:
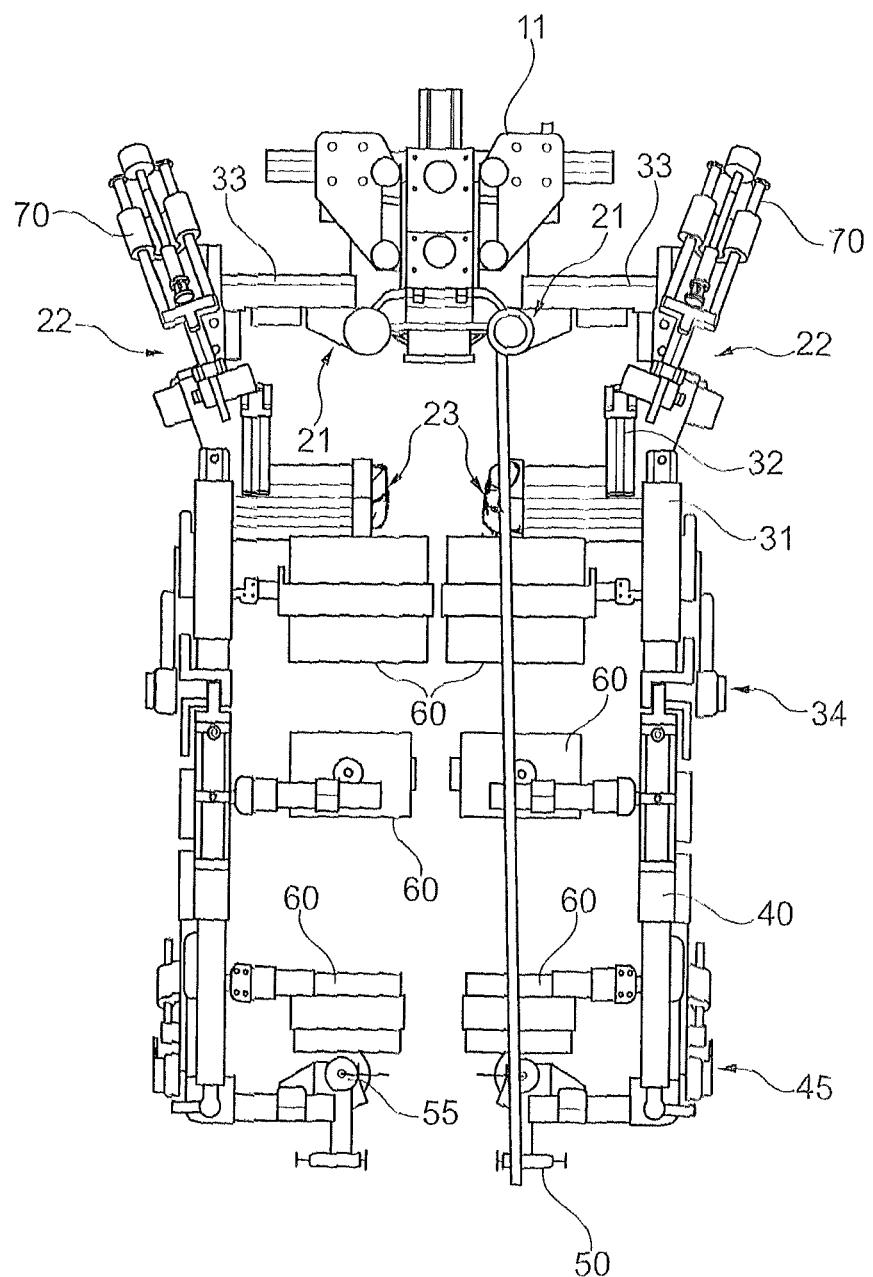
FIG. 10 shows an orthosis in a frontal view in the initial position.

FIG. 10 shows a configuration of the orthosis in the form of a leg orthosis in a frontal view. Apart from the securing device 11, the first joints 21 for performing an abduction and adduction are arranged between the securing device 11 and securing portion 33 on both sides of a center rail. The drives 70 for bringing about a turning of the second joint portion 32 relative to the securing portion 33 about the second joint 22 can similarly be seen, as can the in-line alignment of the pivot axes of the first joint 21 with the third joint 23, which predominantly contributes to the internal rotation and external rotation of the leg orthosis.

The sleeve 60 with the straps for fixing the orthosis to the respective lower extremity can similarly be seen, as can the orthosis knee joints 34, the orthosis ankle joints 45 and the pivot axis 55 for bringing about a pivoting of the foot part 50 in the outward or inward direction.

The invention claimed is:

1. A leg orthosis, comprising:
   a securing device for connecting the leg orthosis to a trunk of the body of an orthosis user;
   at least one articulation device for use with a hip of the orthosis user, the at least one articulation device having at least three joints, each of the at least three joints having a pivot axis, each of the pivot axes of the at least three joints intersecting at a common point and being non-colinear with each other, wherein at least two of the pivot axes are not aligned orthogonally relative to one another;
   a first orthosis component pivotally mounted to the securing device with the at least one articulation device, the first orthosis component configured to be connected to an extremity of the orthosis user.

2. The leg orthosis as claimed in claim 1, wherein the at least one articulation device is assigned at least one drive or energy store.

3. The leg orthosis as claimed in claim 2, wherein a degree of freedom of the pivot axis of one of the at least three joints does not influence degrees of freedom of the pivot axes of the other joints.

4. The leg orthosis as claimed in claim 1, wherein the pivot axes are configured to intersect at a point of rotation of a hip joint of the orthosis user.

5. The leg orthosis as claimed in claim 1, wherein the securing device is configured to connect the leg orthosis to a pelvis, an area of an abdomen or a waist of the orthosis user, and the first orthosis component is designed as an upper leg rail.

6. The leg orthosis as claimed in claim 1, wherein the first orthosis component has a number of portions that are connected to one another in an articulated manner.

7. The leg orthosis as claimed in claim 1, wherein at least one further orthosis component is secured in an articulated manner on the first orthosis component.

8. The leg orthosis as claimed in claim 7, wherein the at least one further orthosis component is formed such that it is configured to connect to the extremity.

9. The leg orthosis as claimed in claim 7, further comprising joints between the first orthosis component and the at least one further orthosis component, and pivot axes of the joints between the first orthosis component and the at least one further orthosis component are configured to be aligned with the joint axes of the extremity when the leg orthosis is in the fitted state.

10. The leg orthosis as claimed in claim 1, wherein the pivot axes of the at least three joints each have a single degree of freedom.

11. The leg orthosis as claimed in claim 1, wherein a pivoting range of the at least three joints is adjustable.

12. The leg orthosis as claimed in claim 1, wherein one of the pivot axes is adapted to enable an extension and flexion of a hip of the orthosis user and the at least one articulation device is assigned a drive that is effective about this pivot axis.

13. The leg orthosis as claimed in claim 1, wherein moments about a non-driven axis or a number of non-driven axes have no influence on the pivot axes.

14. The leg orthosis as claimed in claim 1, wherein, when one of the pivot axes is driven, the other pivot axes are not driven and no torque is applied to the other pivot axes.

15. The leg orthosis of claim 1, wherein the pivot axes of the at least three joints define three different degrees of freedom for the at least one articulation device at the common point.

16. A leg orthosis, comprising:
   a securing device for connecting the leg orthosis to a trunk of the body of an orthosis user;
   at least one articulation device for use with a hip of the orthosis user, the at least one articulation device having at least three joints, each of the at least three joints having a pivot axis, each of the pivot axes of the at least three joints intersecting at a common point and being non-colinear with each other, wherein when one of the pivot axes is driven, the other pivot axes are not driven and no torque is applied to the other pivot axes;
   a first orthosis component pivotally mounted to the securing device with the at least one articulation device, the first orthosis component configured to be connected to an extremity of the orthosis user.

17. The leg orthosis of claim 16, wherein the pivot axes of the at least three joints define three different degrees of freedom for the at least one articulation device at the common point.

18. A leg orthosis, comprising:
   a securing device for connecting the leg orthosis to a trunk of the body of an orthosis user;
   at least one articulation device for use with a hip of the orthosis user, the at least one articulation device having at least three joints, each of the at least three joints having a pivot axis, each of the pivot axes of the at least three joints configured to intersect at a hip joint of the orthosis user, wherein moments about at least one non-driven axis have no influence on the pivot axes;
   a first orthosis component pivotally mounted to the securing device with the at least one articulation device, the first orthosis component configured to be connected to an extremity of the orthosis user.

19. The leg orthosis of claim 18, wherein the pivot axes are configured to define three independent degrees of freedom for the at least one articulation device at the hip joint.

\* \* \* \* \*